(12) United States Patent
Choe (10) Patent No.: US 11,589,804 B1
(45) Date of Patent: Feb. 28, 2023

(54) METHODS AND APPARATUS FOR RECOMMENDING CARE DEVICE FOR USERS

(71) Applicant: LULULAB INC., Seoul (KR)

(72) Inventor: Yongjoon Choe, Seoul (KR)

(73) Assignee: LULULAB INC., Seoul (KR)

( * ) Notice: Subject to any disclaimer, the term of this patent is extended or adjusted under 35 U.S.C. 154(b) by 0 days.

(21) Appl. No.: 17/732,890

(22) Filed: Apr. 29, 2022

(30) Foreign Application Priority Data

Jan. 5, 2022 (KR) .................. 10-2022-0001687

(51) Int. Cl.
*A61B 5/00* (2006.01)
*G06T 7/00* (2017.01)
(Continued)

(52) U.S. Cl.
CPC ............ *A61B 5/441* (2013.01); *A61B 5/0077* (2013.01); *A61B 5/442* (2013.01); *A61B 5/443* (2013.01);
(Continued)

(58) Field of Classification Search
CPC ....... A61B 5/441; A61B 5/0077; A61B 5/442; A61B 5/443; A61B 5/444; A61B 5/445;
(Continued)

(56) References Cited

U.S. PATENT DOCUMENTS 5,544,649 A * 8/1996 David .................... G16H 80/00
600/587
2003/0065578 A1 * 4/2003 Peyrelevade ........... G06T 11/00
705/26.7
(Continued)

FOREIGN PATENT DOCUMENTS

KR 10-2019-0033257 A 3/2019
KR 10-2261321 B1 6/2021
(Continued)

OTHER PUBLICATIONS

Written Decision on Registration dated Apr. 14, 2022 from the Korean Patent Office in Korean Application No. 10-2022-0001687.

*Primary Examiner* — Molly Wilburn
(74) *Attorney, Agent, or Firm* — Sughrue Mion, PLLC (57) ABSTRACT

Disclosed is a care device recommendation server providing a service for recommending a skin care device for a user, the care device recommendation server including: a data management unit configured to obtain face images of the user from a shin measurement device including a camera and a display; a skin condition determination unit configured to determine a first skin condition of the user corresponding to a first time point at which the face images are obtained, based on the obtained the face images; a care device recommendation unit configured to determine the skin care device for the user among a plurality of care devices included in a care device DB based on the determined first skin condition; a care device control value-providing unit configured to provide a first control value of the skin care device corresponding to the first skin condition to each of a user terminal of the user and the skin measurement device; a care device control unit configured to remotely control the care device such that the skin care device is driven by the control value; and a history provision unit configured to provide information about a previous skin condition of the user, which corresponds to each of the face images of the user obtained from the data management unit, to the user terminal.

4 Claims, 7 Drawing Sheets

(51) Int. Cl.
*G16H 50/20* (2018.01)
*G16H 30/40* (2018.01)

(52) U.S. Cl.
CPC .............. *A61B 5/444* (2013.01); *A61B 5/445* (2013.01); *A61B 5/6898* (2013.01); *G06T 7/0012* (2013.01); *G16H 30/40* (2018.01); *G16H 50/20* (2018.01); *G06T 2207/30088* (2013.01)

(58) Field of Classification Search
CPC ................ A61B 5/6898; G06T 7/0012; G06T 2207/30088; G16H 30/40; G16H 50/20
See application file for complete search history.

(56) References Cited

U.S. PATENT DOCUMENTS

| | | | | |
|---|---|---|---|---|
| 2003/0065588 | A1* | 4/2003 | Rubinstenn | G06Q 30/0633 |
| | | | | 705/26.8 |
| 2006/0282288 | A1* | 12/2006 | Rodriguez | G06Q 10/06375 |
| | | | | 705/2 |
| 2008/0194928 | A1* | 8/2008 | Bandic | A61B 5/443 |
| | | | | 600/306 |
| 2009/0105605 | A1* | 4/2009 | Abreu | A61B 5/4076 |
| | | | | 600/549 |
| 2010/0185064 | A1* | 7/2010 | Bandic | A61B 5/444 |
| | | | | 600/306 |
| 2013/0179298 | A1* | 7/2013 | Segman | G16H 20/10 |
| | | | | 705/26.7 |
| 2016/0125228 | A1* | 5/2016 | Son | A61B 5/1176 |
| | | | | 382/118 |
| 2016/0262624 | A1* | 9/2016 | Nakajima | A61B 5/7278 |
| 2017/0345144 | A1* | 11/2017 | Pai | A61B 5/445 |
| 2018/0033205 | A1* | 2/2018 | Kong | G06V 40/164 |
| 2019/0099613 | A1* | 4/2019 | Estes | A61N 5/0616 |
| 2019/0125249 | A1* | 5/2019 | Rattner | G16H 40/67 |
| 2019/0366119 | A1* | 12/2019 | Kim | A61B 5/7267 |
| 2020/0146622 | A1* | 5/2020 | Bock | G06T 7/0016 |
| 2020/0375526 | A1* | 12/2020 | Oh | A61B 5/1176 |
| 2020/0383629 | A1* | 12/2020 | Yoo | A61B 5/742 |
| 2021/0022662 | A1* | 1/2021 | Hyun | G16H 30/20 |
| 2021/0182705 | A1* | 6/2021 | Bates | A61B 5/442 |

FOREIGN PATENT DOCUMENTS

| | | |
|---|---|---|
| KR | 10-2285912 B1 | 8/2021 |
| KR | 10-2314167 B1 | 10/2021 |

\* cited by examiner

METHODS AND APPARATUS FOR RECOMMENDING CARE DEVICE FOR USERS

CROSS REFERENCE TO RELATED APPLICATIONS

This application claims priority to Application No. 10-2022-0001687 filed in Korea on Jan. 5, 2022, the entire contents of which is hereby incorporated by reference.

FIELD OF INVENTON

The present invention relates to a method of recommending a care device for users and a method therefor, and more particularly to a method of determining a user's skin condition, recommend a care device for improving the determined skin condition, and providing an optimal control value of the care device for improving a skin condition when using the recommended care device; and a device therefor.

BACKGROUND OF INVENTION

As interest in beauty increases, interest in skin beauty at users' faces is recently increasing. In particular, skin condition measurement devices that captures she user's facial skin and analyses various skin problems (e.g., wrinkles, pores, acne, etc.) on the user's face are being developed.

Recently, a skin condition measuring device has been used as one component of a skin comprehensive care system, such as recommendation of cosmetics, based on skin condition measurement results. In particular, based on the development of IoT technology and the accumulation of big data, R&D is being actively conducted on a system that provides a device for measuring skin condition and recommending customized products.

However, there is no commercially available technology for measuring the skin condition, providing the optimal control value of a skin care device for improving the skin condition of a user, and, when the skin care device is used, simultaneously providing an expected skin improvement condition.

SUMMARY OF INVENTION

Technical Problem to be Solved

Therefore, the present invention has been made in view of the above problems, and it is one object of the present invention to provide a method of determining a user's skin condition using a user's face image obtained through a skin measurement device.

It is another object of the present invention to provide a method of determining a care device for improving the determined user's skin condition.

It is yet another object of the present invention to provide information about an improved skin condition of a user when using the care device.

Technical Solution

In accordance with an aspect of the present invention, the above and other objects can be accomplished by the provision of a care device recommendation server providing a service for recommending a skin care device for a user, the care device recommendation server including: a data management unit configured to obtain face images of the uses from a skin measurement device including a camera and a display; a skin condition determination unit configured to determine a first skin condition of the user corresponding to a first time point at which the face images are obtained, based on the obtained the face images; a care device recommendation unit configured to determine the skin care device for the user among a plurality of care devices included in a care device DB based on the determined first skin condition; a care device control value-providing unit configured to provide a first control value of the skin care device corresponding to the first skin condition to each of a user terminal of the user and the skin measurement device; a care device control unit configured to remotely control the care device such that the skin care device is driven by the control value; and a history provision unit configured to provide information about a previous skin condition of the user, which corresponds to each of the face images of the user obtained from the data management unit, to the user terminal.

In accordance with various embodiments, the history provision unit may list previous skin condition images of the user in time series and provide the listed previous skin condition images to the user terminal, may calculate composite scores on skin conditions corresponding to the previous skin condition images, and may determine total scores of the calculated individual scores as the composite scores and provide the determined composite scores to the user terminal, wherein when the composite scores are calculated, an individual score for each item of skin wrinkles, skin tone, pore state, pigmentation, dark circles, redness, and dead skin state of the user is calculated.

In accordance with various embodiments, the care device recommendation server may further include a skin change prediction unit for predicting a second skin condition of the user corresponding to a second time point after a preset time from the first time point, wherein the skin change prediction unit determines the second skin condition of the user corresponding to the second time point based on the first skin condition, a seasonal change between the first time point and the second time point, and an aging degree corresponding to an age of the user up to the second time point, determine a first date corresponding to the first time point and a second date corresponding to the second time point, calculates an expected change in temperature and an expected change in humidity based on a first annual average weather corresponding to the first date and a second annual average weather corresponding to the second date, and determines a first skin change degree of the user according to the seasonal change based on the calculated expected temperature change and the calculated expected humidity change.

In accordance with various embodiments, the skin change prediction unit may determine an expected aging degree of the user from the first time point to the second time point based on an age of the user and an average aging rate corresponding to the user's age, and may determine a second skin change degree according to aging of the user based on the determined expected aging degree.

In accordance with various embodiments, the care device recommendation server may include an improvement state-providing unit for providing information about an improved skin condition of the user, expected when the skin care device is used with the first control value, to the user terminal, wherein the improvement state-providing unit obtains an input signal, which indicates a period of use of the skin care device, from the user terminal, determines a user's skin condition improvement degree predicted when the skin care device is used for the period, and provides information about an improved skin condition of the user based on the skin condition improvement degree to a user terminal.

In accordance with various embodiments, the improvement state-providing unit may determine a skin improvement degree of each of other users based on review images among information about skin improvement of the users using the skin care device obtained from a care device company, may determine an average skin improvement degree of the users corresponding to the use period based on the skin improvement degree of each of the users, and may determine the predicted user's skin condition improvement degree based on the average skin improvement degree of the users.

In accordance with various embodiments, the skin change prediction unit may determine the second skin condition of the user based on the first skin condition, the first skin change degree, the second skin change degree, and the skin condition improvement degree, and the care device control value-providing unit may provide may provide a second control value of the skin care device corresponding to the second skin condition to the user terminal.

In accordance with various embodiments, the skin change prediction unit may determine the second skin change degree using the average skin aging estimation model, the average skin aging estimation model may be supervised and learned in advance by using training data of using a first feature vector, obtained by transforming features of facial images obtained from a plurality of people, as an input value; and a second feature vector obtained by transforming features of average facial images, aged for a preset period, obtained from the people as an output value, and the skin change prediction unit 104 convert the features of the face image of the user at the first time point into an input vector to input into the supervised and learned average skin aging estimation model, may change an output vector obtained as an output of the supervised and learned average skin aging estimation model to obtain features of an aged face image of the user during the preset period, may generate an aged face image of the user using the features of the aged face image, add may determine the second skin change degree based on the aged face image of the user during the preset period.

Effect of Invention

In accordance with various embodiments of the present specification, a more accurate face image of a user can be obtained by using a professional skin measurement device.

In addition, according to various embodiments, a user's skin condition can be accurately diagnosed by analyzing the user's face image based on AI and big data.

In addition, according to various embodiments, a user's skin condition can be improved by recommending a skin care device necessary for a user.

In addition, according to various embodiments, a user can be efficiently with skin improvement effect by not only simply recommending a skin care device, but also simultaneously providing an optimal care device control value improving for a skin condition.

Further, various effects directly or indirectly identified through the present specification can be provided.

BEST MODE

Since the present invention may be applied with various modifications and may have various embodiments, exemplary embodiments and drawings of the present invention are intended to be explained and exemplified. However, these exemplary embodiments and drawings are not intended to limit the embodiments of the present invention to particular modes of practice, and all changes, equivalents, and substitutes that do not depart from the spirit and technical scope of the present invention should be understood as being encompassed in the present invention. Like reference numerals refer to like elements in describing each drawing.

The terms such as "first," "second," "A" and "B" are used herein merely to describe a variety of constituent elements, but the constituent elements are not limited by the terms. The terms are used only for the purpose of distinguishing one constituent element from another constituent element. For example, a first element may be termed a second element and a second element may be termed a first element without departing from the teachings of the present invention. The term "and/or" includes any or all combinations of one or more of the associated listed items.

It should be understood that when an element is referred to as being "connected to" or "coupled to" another element, the element may be directly connected or coupled to the other element or intervening elements may be present. In contrast, when an element is referred to as being "directly connected to" or "directly coupled to" another element, there are no intervening elements present.

The terms used in the present specification are used to explain a specific exemplary embodiment and not to limit the present inventive concept. Thus, the expression of singularity in the present specification includes the expression of plurality unless clearly specified otherwise in context. Also, terms such as "include" or "comprise" should be construed as denoting that a certain characteristic, number, step, operation, constituent element, component or a combination thereof exists and not as excluding the existence of or a possibility of an addition of one or more other characteristics, numbers, steps, operations, constituent elements, components or combinations thereof.

Unless otherwise defined, all terms (including technical and scientific terms) used herein have the same meaning as commonly understood by one of ordinary skill in the art to which this disclosure belongs. It will be further understood that terms, ouch as those defined in commonly used dictionaries, should be interpreted as having a meaning that is consistent with their meaning in the context of the relevant art and will not be interpreted in an idealized or overly formal sense unless expressly so defined herein.

Hereinafter, the present invention will be described in detail by explaining exemplary embodiments of the invention with reference to the attached drawings.

Figure 1:
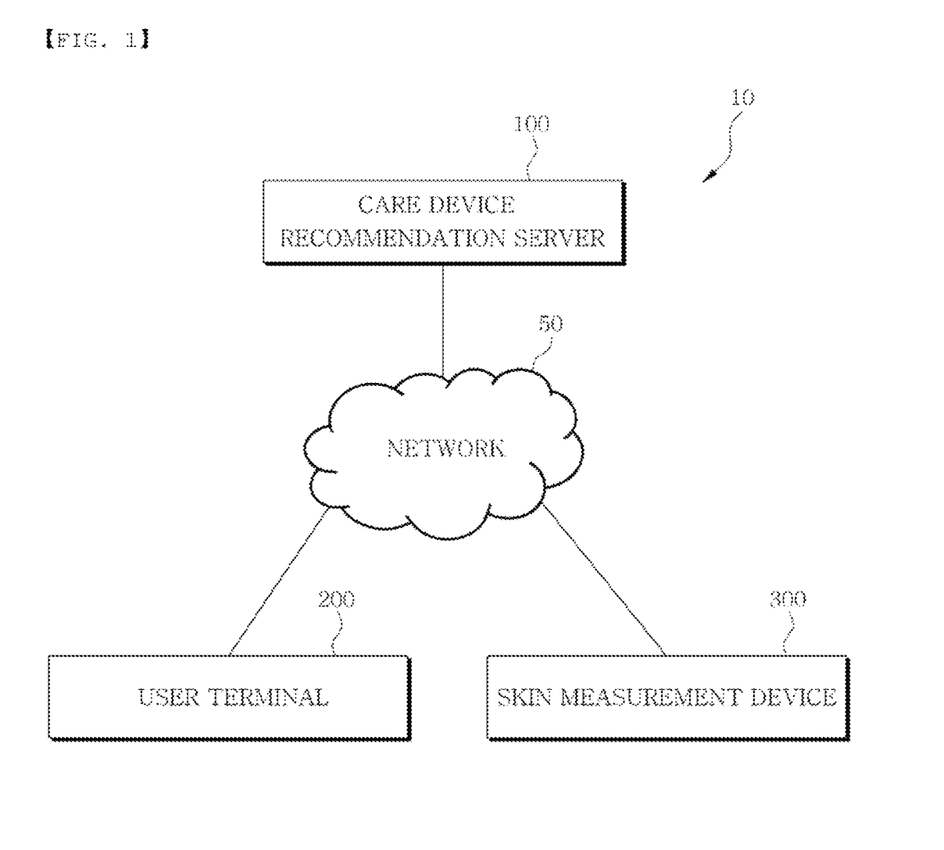
FIG. 1 illustrates a care device recommendation system according to an embodiment of the present invention.

FIG. 1 illustrates a care device recommendation system 10 according to an embodiment of the present invention. Referring to FIG. 1, the care device recommendation system 10 may include a care device recommendation server 100, a user terminal 200, a skin measurement device 300, and the like. Operations described below may be performed through a platform (e.g., a web page and/or a kind of application) controlled by the care device recommendation server 100.

The care device recommendation server 100 may determine a user's skin condition based on a user's face image, may determine a customized skin care device to be recommended to the user according to the determined skin condition, and may provide information about the determined skin care device to the user terminal 200. The skin care device may include a care device provided from a care device company contracted with the care device recommendation server 100, a care device manufactured and provided by the care device recommendation server 100 by itself, and the like The skin condition may include skin color, the moisture, oil, sebum, pH level, sensitivity, elasticity, and wrinkles of the skin, skin tone, pore conditions, pigmentation, dark circles, redness, keratin conditions, and the like.

The care device recommendation server 100 may conclude a contract with a plurality of care device companies. The care device recommendation server 100 may obtain information about a care device, provided by each of the plurality of the contracted care device companies, from the care device company. The care device recommendation server 100 may store information about the obtained care device in a care device DB. For example, the information about the care device may include the price, AS period, use, efficacy, image, use method, size, weight, use mode, use stage, and strength control of the care device, and the like.

The care device recommendation server 100 may obtain a user's face image through the skin measurement device 300 interlocked with the care device recommendation server 100. The care device recommendation server 100 may obtain a hair image, a scalp image, etc. as well as a face image through the skin measurement device 300.

The skin measurement device 300 may be implemented in various shapes. For example, the skin measurement device 300 has a mask shape or a bar shape.

The user terminal 200 may be a communicationable desktop computer, a laptop computer, a notebook, a smart phone, a tablet PC, a mobile phone, a smart watch, a smart glass, an e-book reader, a portable multimedia player (PMP), a portable game console, a navigation device, a digital camera, a digital multimedia broadcasting (DMB) player, a digital audio recorder, a digital audio player, a digital video recorder, a digital video player, and personal digital assistant (PDA), or the like.

Each of the care device recommendation server 100, the user terminal 200 and the skin measurement device 300 may be connected to the communication network 50 to transmit and receive data between each other through the communication network 50. For example, various types of wired or wireless networks such as Local Area Network (LAN), Metropolitan Area Network (MAN), Global System for Mobile Network (GSM), Enhanced Data GSM Environment (EDGE), High Speed Downlink Packet Access (HSDPA), Wideband Code Division Multiple Access (W-CDMA), Code Division Multiple Access (CDMA), Time Division Multiple Access (TDMA), Bluetooth, Zigbee, Wi-Fi, Voice over Internet Protocol (VoIP), LTE Advanced, IEEE802.16m, wireless MAN-Advanced, HSPA+, 3GPP Long Term Evolution (LTE), mobile WiMAX (IEEE 802.16e), formerly EV-DO Rev. C (UMB), flash-OFDM, iBurst and MBWA (IEEE 802.20) systems, HIPERMAN, Beam-Division Multiple Access (BDMA), World Interoperability for microwave Access (WI-MAX) and 5G may be used as the communication network 50.

Figure 2:
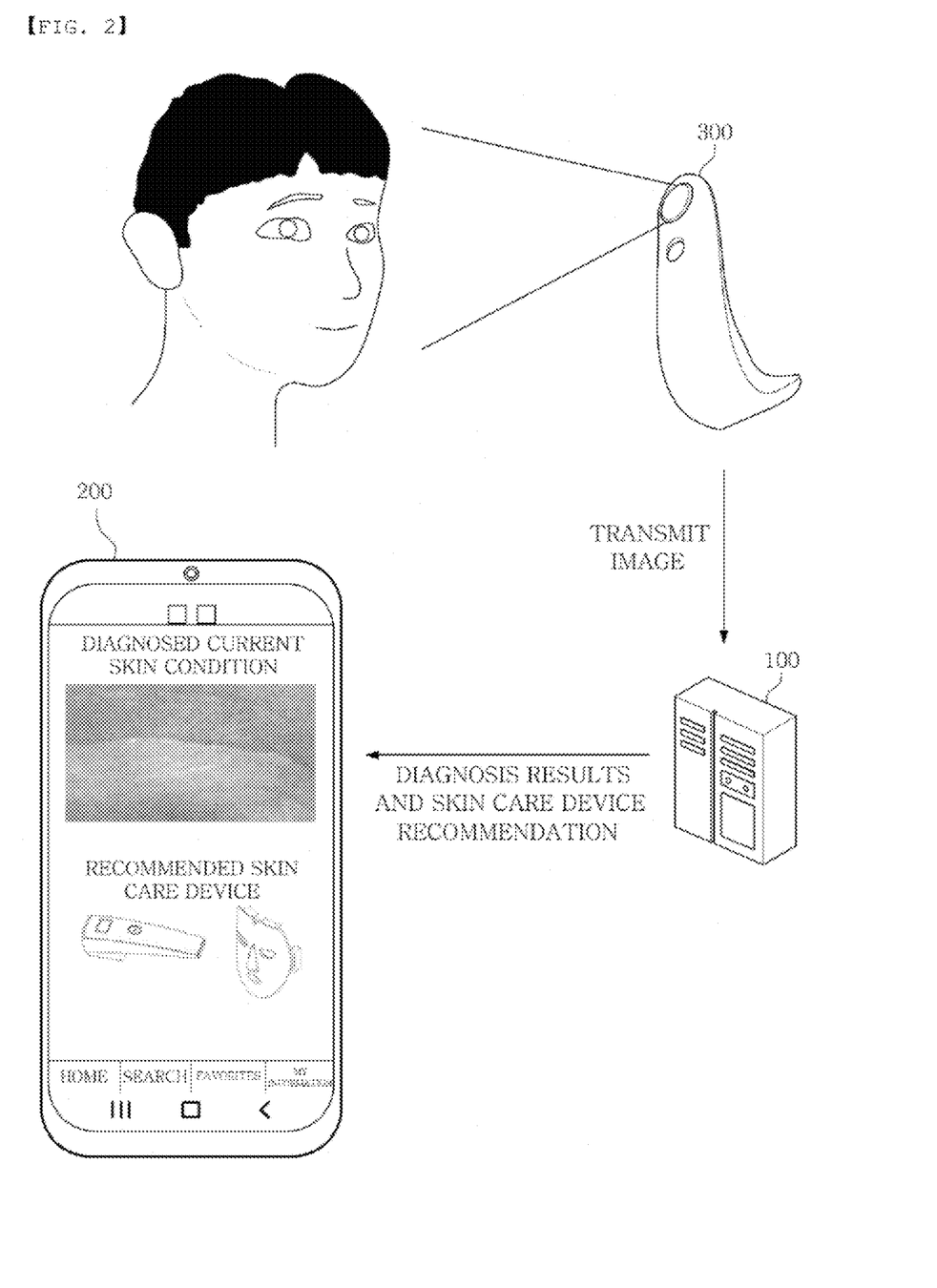
FIG. 2 illustrates an overall flow of providing a care device recommendation service to a user by a care device recommendation system.

FIG. 2 illustrates an overall flow of providing a care device recommendation service to a user by a care device recommendation system.

Referring to FIG. 2, a user may take an image of his/her face using the skin measurement device 300. The skin measurement device 300 may transmit the photographed face image of the user to the care device recommendation server 100. The care device recommendation server 100 may obtain the user's face image through the skin measurement device 300. The care device recommendation server 100 may analyze the user's face image received in the skin measurement device 300, may determine a user's skin condition according to the analysis result, and may determine a skin care device to be recommended to the user according to the determined skin condition.

The measurement device 300 may be equipped with at least one camera, and the camera may be in the form of a camera module including a flash, a plurality of lenses, an AF module, an OIS module, an image sensor, an image signal processor, and the like. The skin measurement device 300 may be controlled by the care device recommendation server 100. For example, a camera magnification, changed camera type, light source intensity, light source and/or light source direction, and the like of the skin measurement device 300 may be determined by a user or the care device recommendation server 100. For example, the care device recommendation server 100 may transmit a changed photographing parameter value and a re-photography request signal to the skin measurement device 300 when the user's face image obtained from the skin measurement device 300 does not satisfy a preset condition for determining a user's skin condition. The skin measurement device 300 may receive a skin care device control value, described below, from a care device control value providing unit 106, and the provided skin care device control value may be displayed through a display mounted on one surface on the skin measurement device 300.

The user terminal 200 may display the user's skin condition information and/or skin care device information, received from the care device recommendation server 100, through a display. For example, the user terminal 200 may display the user's skin condition image (e.g., image showing detailed wrinkles), determined based on the face image taken through the skin measurement device 300, through a display, and may display an image of a care device recommended to improve the skin condition through a display. An interface displayed through a display of the user terminal 200 may be further described with reference to FIGS. 4a and 4b below.

The care device may be driven based on a control value determined by a user. Alternatively, the care device may be linked to the care device recommendation server 100, and may be operated by a control value determined by the care device recommendation server 100.

Figure 3:
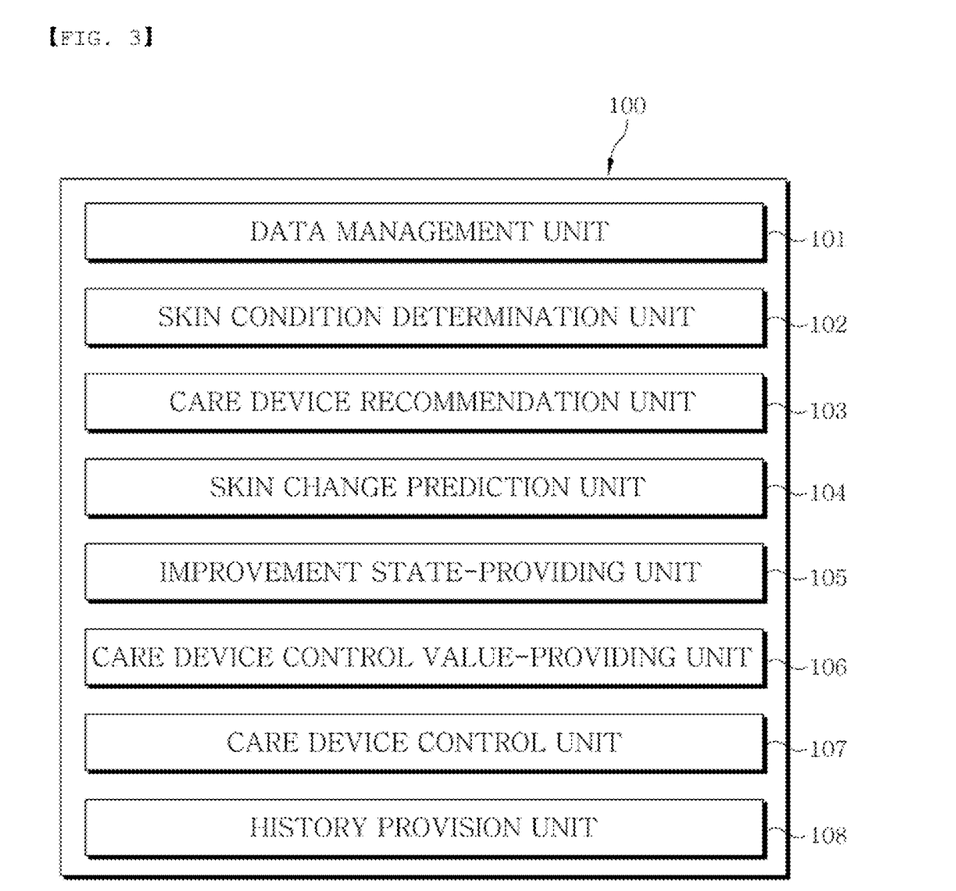
FIG. 3 illustrates main components of the care device recommendation server.

FIG. 3 illustrates main components of the care device recommendation server 100.

Referring to FIG. 3, the care device recommendation server 100 may include a data management unit 101, a skin condition determination unit 102, a care device recommendation unit 103, a skin change prediction unit 104, an improvement state-providing unit 105, a care device control value-providing unit 106, and the like.

The data management unit 101 may obtain the user's face image from the skin measurement device 300 and may store the obtained face image in a user DB.

A skin condition determination unit 102 may determine the skin condition of the user based on the obtained user's face image. For example, the skin condition may include skin color, the moisture, oil, sebum, pH level, sensitivity, elasticity, and wrinkles of the skin, skin tone, pore conditions, pigmentation, dark circles, redness, keratin conditions, and the like. The skin condition determination unit 102 may determine a user's skin condition using the user's face image obtained through skin analysis kiosk and the user terminal 200 as well as the user's face image obtained from the skin measurement device 300. In other words, although FIG. 2 illustrates the skin measurement device 300 as a portable device, but this is only an example. The skin measurement device 300 may be a skin analysis kiosk as well as a portable device. The, kiosk-type skin measurement device 300 may include a camera, a display, and the like.

The care device recommendation unit 103 may determine skin care devices that are capable improving the determined user's skin condition. The care device recommendation unit 103 may generate a recommendation list of skin care devices to be recommended to a user based on the determined skin care devices. The skin care devices determined by the care device recommendation unit 103 may be linked to be driven the care device recommendation server 100.

The skin change prediction unit 101 may determine a user's second skin condition at a second time point after a specific period from a first time point that is a time point at which the user's face image is acquired. a user's face image. In other words, the skin condition determination unit 102 may determine a user's first skin condition at the first time point that is a time point at which the face image is acquired, and the skin change prediction unit 104 may predict or determine the user's second skin condition corresponding to the second time point based on i) the first skin condition, ii) a seasonal change (e.g., temperature change and/or humidity change) between the first time point and the second time point, and iii) an aging degree or aging rate up to the second time point corresponding to the age of the user.

The improvement state-providing unit 105 may determine a user's skin condition improvement degree predicted when the user uses the determined skin care device by the care device recommendation unit 103, and may provide the determined skin condition improvement degree to the user terminal 200.

The care device control value-providing unit 106 provides a control value for operating the skin care device determined to be recommended to the user, and, in particular, may provide an optimal control value for improving a user's skin condition to the user terminal 200. The care device control value-providing unit 106 may provide the control value to the user terminal 200, and a care device user may operate the skin care device with an optimal control value for improving a skin condition based on the control value provided through the user terminal 200. The care device control value may be a value related to at least a care device operation time, a care device operation mode, a care device operation intensity, and the like.

A care device control unit 107 may remotely control the care device such that the care device is driven by the control value. In other words, the care device control unit 107 may control the skin care device such that the skin care device is driven by a care device operation mode, care device operation time, and care device operation intensity for improving the first skin condition of a user.

A history provision unit 108 may store, based on user's face images obtained from the skin measurement device, information about user's previous skin condition corresponding to each of the face images, and may provide information about the stored skin condition to the user terminal 200. The face images may be obtained every preset period. The history provision unit 108 may list images related to the user's skin condition in chronological order and provide the listed images to the user terminal 200 such that the user can directly feel a skin change due to use of the skin care device.

The history provision unit 108 may calculate composite scores on the skin condition corresponding to the images, may generate a graph according to a score change between the calculated composite scores, and may provide the generated graph to the user terminal 200. The history provision unit 108 may calculate an individual score for each item, such as the skin wrinkles, skin tone, pore state, pigmentation, dark circles, redness, and dead skin state, of the user, and may determine a total score of the individual scores calculate for the respective item as a composite score for the skin condition. The history provision unit 108 may calculate a change in the composite scores between the images listed in chronological order, and may provide the information about the calculated composite score change to the user terminal 200. When calculating the composite score change, the history provision unit 108 does not simply calculate a difference between a first composite score corresponding to a first image and a second composite score to corresponding to a second image, but may determine the weight of a first item corresponding to a lowest score in the first composite score as the highest and may determine the weight of a second item corresponding to a highest score in the first composite score as lowest. The history provision unit 108 may calculate an individual score difference between items, may multiply the individual score difference by the weight, and may determine a total score of the individual score differences multiplied by the weight as a composite score change. The second image may be a first image acquired after Line time-series at which the first image is acquired.

The history provision unit 108 may calculate a change in the composite scores through Equation 1 below:

$$S = \sum_{i=1}^{i=n}((i_a - i_b) \times w_i)$$ [Equation 1]

where S denotes a change in the composite scores, n denotes the number of individual items (wrinkles, skin tone, pore state, pigmentation, dark circles, redness, dead skin state, etc.) for calculating a composite score on a skin condition, $i_a$ denotes a score of a i-th item for calculating a composite score for a skin condition corresponding to the first image, $i_b$ denotes a score of a i-th item for calculating a composite score for a skin condition corresponding to the second image, and $w_i$ denotes a weight for a i-th item.

Figure 4A:
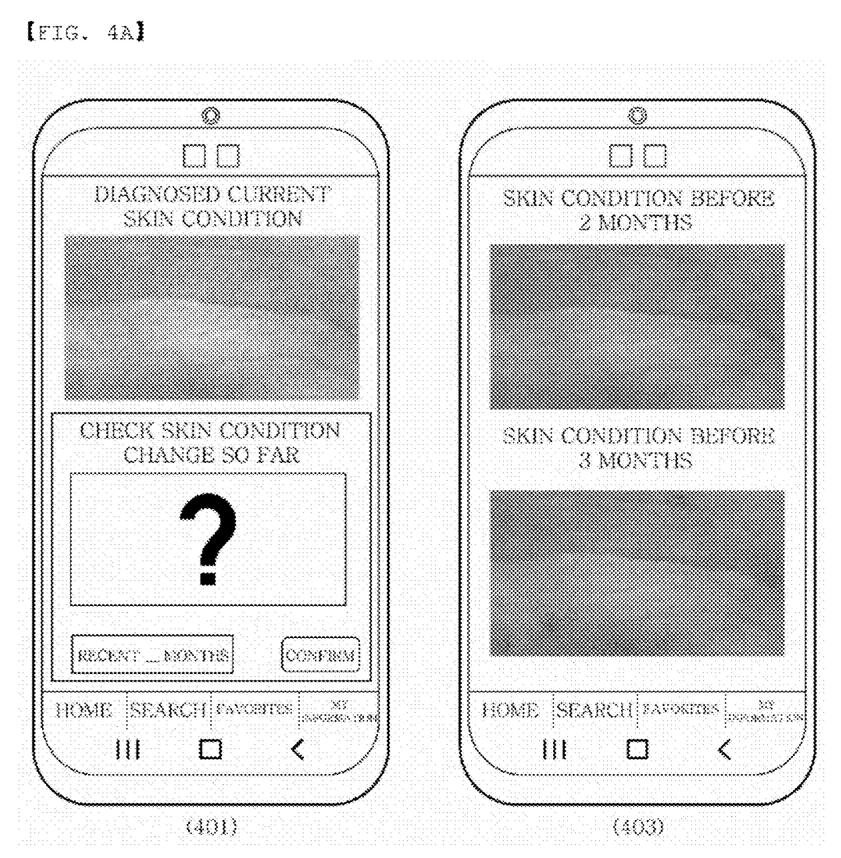
FIG. 4a illustrates a user's skin condition measurement history measured through a user terminal.

FIG. 4*a* illustrates a user's skin condition measurement history measured through a user terminal.

Examining reference numeral 401 of FIG. 4*a*, the user terminal 200 may provide a user interface indicating a current skin condition of a user. The user terminal 200 may display a user interface indicating information about a user's skin condition when the skin care device determined by the care device recommendation unit 103 is used for a specific period. The user terminal 200 may obtain a user input signal indicating the use period. For example, the user terminal 200 may obtain a user input signal of inputting 3 months. The user terminal 200 may provide or transmit the obtained user input signal to the history provision unit 108.

Examining reference numeral 403 of FIG. 4a, the history provision unit 108 may obtain an input signal indicating a period of use of the skin care device from the user terminal 200. The history provision 108 may provide information about the user's previous skin condition, which corresponds to each of the user's face images obtained during the use period, to the user terminal 200 based on the input signal, which indicates the use period of the skin care device, obtained from the user terminal 200. The information about the previous skin condition may include images regarding the user's previous skin conditions from a time point before the use period to the present time based on the current time point. For example, the history provision unit 108 may provide an image regarding a user's previous skin condition to the user terminal 200 when the skin care device is used for 3 months.

Figure 4B:
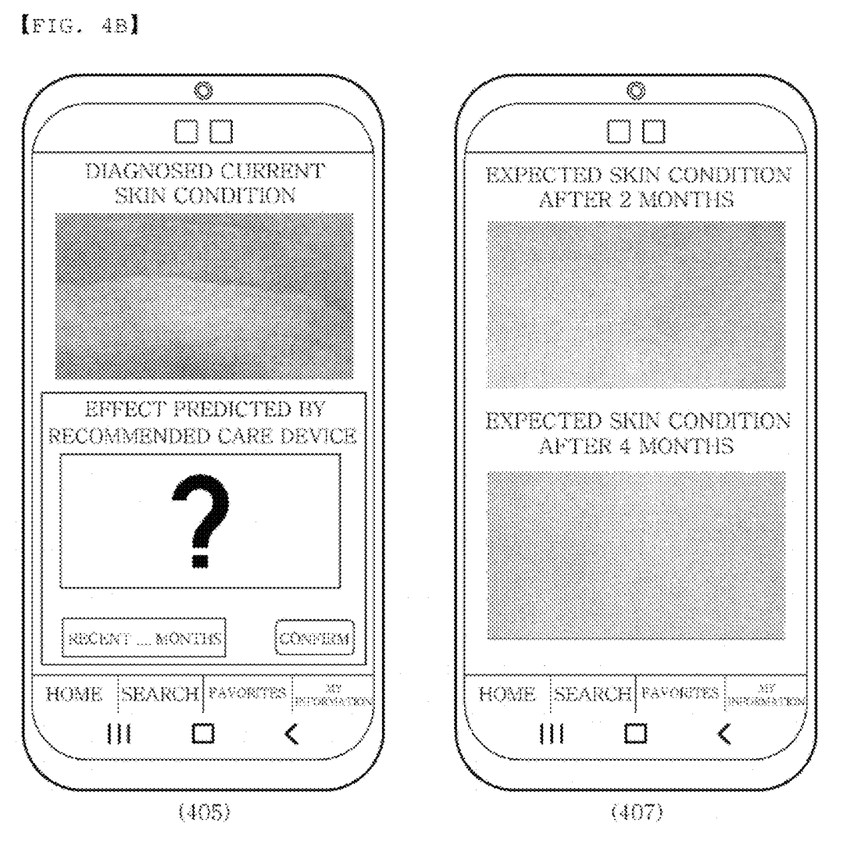
FIG. 4b illustrates a current skin condition of a user and an expected effect of using a recommend skin care device through a user terminal.

FIG. 4b illustrates a current skin condition of a user and an expected effect of using a recommend skin care device through a user terminal.

Examining reference numeral 405 of FIG. 4b, the user terminal 200 may provide a user interface indicating a current skin condition of a user. The user terminal 200 may display a user interface indicating an improvement degree of a user's skin condition when the skin care device determined by the care device recommendation unit 103 is used for a specific period. The user terminal 200 may obtain a user input signal indicating the use period. For example, the user terminal 200 may obtain a user input signal of inputting 3 months. The user terminal 200 may provide or transmit the obtained user input signal to an improvement condition provision unit 105.

Examining reference numeral 407 of FIG. 4b, the improvement condition provision unit 105 may obtain an input signal indicating a period of use of the skin care device from the user terminal 200. The improvement condition provision unit 105 may predict a user's skin condition improvement degree during the use period based on the input signal, which indicates the use period of the skin care device, obtained from the use terminal 200, and may provide information about the user's skin improvement state to the user terminal 200 based on the predicted skin condition improvement degree. The information about improvement state may include images regarding a predicted skin condition of the user after the use period. For example, the improvement condition provision unit 105 may provide an image regarding a user's predicted skin condition to the user terminal 200 when the recommended care device is used for 2 months.

Figure 5:
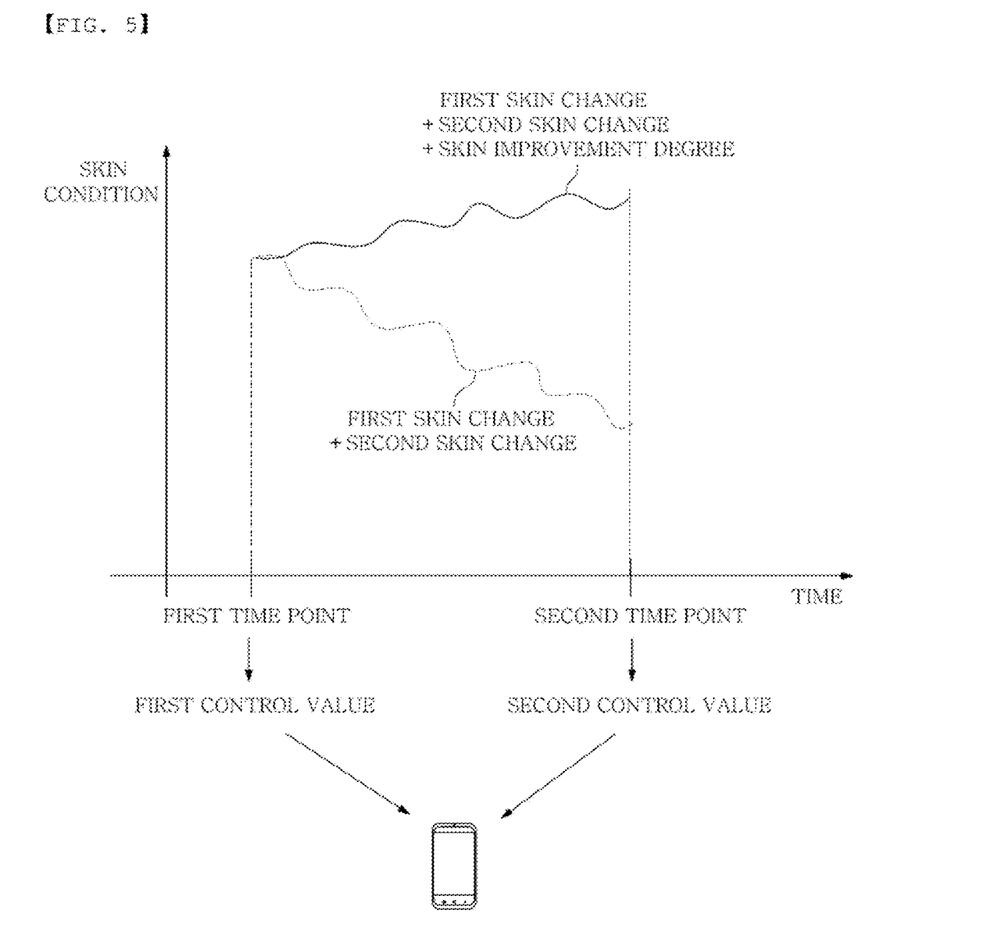
FIG. 5 illustrates provision of a care device control value to a user terminal by a care device control value-providing unit.

FIG. 5 illustrates provision of a care device control value to a user terminal by a care device control value-providing unit.

The care device recommendation server 100 not only may determine a skin care device for improving a user's skin condition through the care device recommendation unit 103, but also may provide a control value of the skin care device for improving a user's skin condition to the user terminal 200 through the care device control value-providing unit 106.

In an embodiment, the skin change prediction unit 104 may determine a user's second skin condition at a second time point after elapse of the use period from a first time point that is a time point at which the user's face image is acquired. a user's face image. In other words, the skin condition determination unit 102 may determine a user's first skin condition at the first time point that is a time point at which the face image is acquired, and the skin change prediction unit 104 may predict or determine the user's second skin condition corresponding to the second time point based on i) the first skin condition, ii) a seasonal change (e.g., temperature change and/or humidity change) between the first time point and the second time point, and iii) an aging degree or aging rate up to the second time point corresponding to the age of the user.

The skin change prediction unit 101 may determine a first date corresponding to the first time point; and a second date corresponding to the second time point, and may calculate an expected change in temperature and an expected change in humidity based on a first annual average weather corresponding to the first date; and a second annual average weather corresponding to the second date. The skin change prediction unit 104 may determine a user's first skin change degree based on the calculated expected temperature change and the calculated expected humidity change. In other words, the skin change prediction unit 104 may determine a first skin change degree according to a determined seasonal change. For example, in seasons (e.g., winter) or months (e.g., November to February) when temperature and humidity are low, the skin wrinkles may worsen as the skin becomes dry. As another example, the skin wrinkles may be reduced during a season (e.g., summer) or a month (e.g., May to August) when temperature and humidity are high.

The skin change prediction unit 104 may predict or determine a user's aging degree or aging rate up to a second time point based on the user's age and an aging rate corresponding to the user's age. The skin change prediction unit 104 may determine a second skin change degree according to the aging rate of the user, based on the aging degree or the aging rate.

The skin change prediction unit 104 may determine the second skin change degree according to the aging rate of the user using the average skin aging estimation model. The average skin aging estimation model may be supervised and learned in advance by using training data of using a first feature vector, obtained by transforming features of facial images obtained from a plurality of people, as an input value; and a second feature vector obtained by transforming features of average facial images, aged for a preset period, obtained from the people as an output value.

The, skin change prediction unit 104 may convert the features of the face image of the user at the first time point into an input vector to input into the supervised and learned average skin aging estimation model, may change an output vector obtained as an output of the supervised and learned average skin aging estimation model to obtain features of an aged face image of the user during the preset period, and may generate an aged face image of the user using the features of the aged face image. The skin change prediction unit 104 may determine the second skin change degree based on the aged face image of the user during the preset period.

In another embodiment, the skin change prediction unit 104 may determine a user's second skin condition at a second time point after elapse of the use period from a first time point that is a time point at which the user's face image is acquired. a user's face image. In other words, the skin condition determination unit 102 may determine a user's first skis condition at the first time point that is a time point at which the face image is acquired, and the skin change prediction unit 104 may predict the user's second skin condition based on i) the first skin condition, ii) a seasonal change (e.g., temperature change and/or humidity change) between the first time point and the second time point, iii) an aging degree or aging rate up to the second time point corresponding to the age of the user, and iv) a user's skin condition improvement degree predicted when the skin care device determined to be recommended to the user is used for a specific period from the first time point.

The improvement state-providing unit 105 may determine a user's skin condition improvement degree when the skin care device determined to be recommended to the user is used for a specific period. The data management unit 101 may collect information on skin improvement of other users, who have used the determined skin care device, from a care device company that provides the determined the skin care device. The information on skin improvement may include information on the period of use of the skin care device of other users, wrinkle improvement, elasticity improvement, pigmentation improvement, dark circle improvement, and keratin status improvement. The improvement state-providing unit 105 determine a user's skin condition improvement degree predicted when the skin care device determined to be recommended to the user is used for a specific period, based on the collected information on skin improvement of other users who have used the skin care device.

The skin change prediction unit 104 may determine a user's second skin condition corresponding to the second time point based on the user's first skin condition corresponding to the first time point, the first skin change degree, the second skin change degree, and the skin condition improvement degree.

The care device control value-providing unit 106 may provide may provide a first control value of the skin care device for improving the first skin condition and a second control value of the skin care device for improving the second skin condition to the user terminal 200. The second control value may be different from the first control value.

Figure 6:
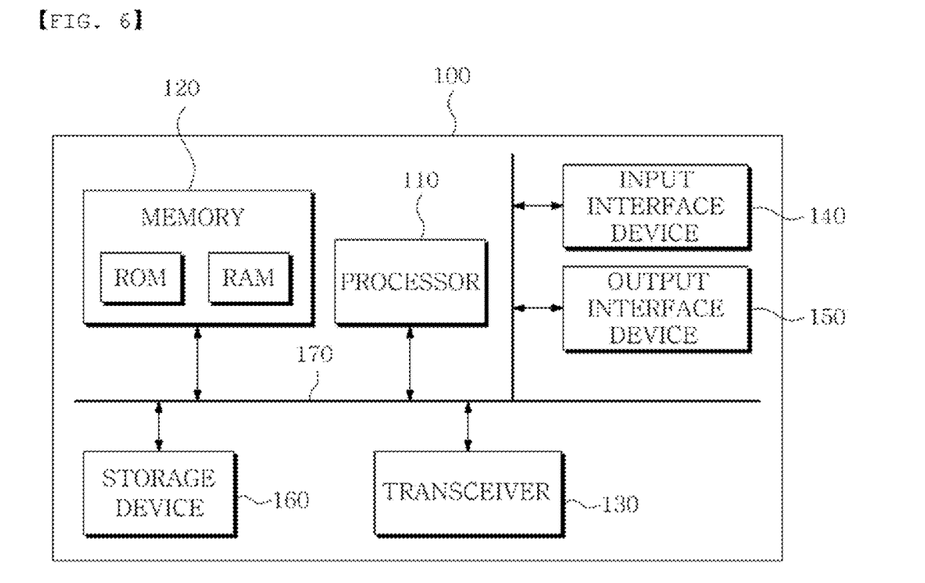
FIG. 6 illustrates the hardware configuration of the care device recommendation server of FIG. 1.

FIG. 6 illustrates the hardware configuration of the care device recommendation server 100 of FIG. 1.

Referring to FIG. 6, the care device recommendation server 100 may include at least one processor 110; and a memory for storing instructions that instruct the at least one processor 110 to perform at least one operation.

The at least one operation may include at least some of the above-described operations or functions of the care device recommendation server 100 and may be implemented in the form of instructions to be performed by the processor 110.

Here, the at least one processor 110 may mean a central processing unit: (CPU), a graphics processing unit (GPU), or a dedicated processor where the methods according to embodiments of the present invention are performed. Each of the memory 120 and the storage device 160 may be configured of at least one of a volatile storage medium and a non-volatile storage medium. For example, the memory 120 may be one of a read only memory (ROM) and a Random access memory (RAM), and the storage device 160 may be a flash-memory, a hard disk drive (HDD), a solid state drive (SSD), various memory cards (e.g., micro SD card), or the like.

In addition, the care device recommendation server 100 may include a transceiver 130 for performing communication through a wireless network. In addition, the care device recommendation server 100 may further include an input interface device 140, an output interface device 150, a storage device 160, and the like. Each of the components included in the care device recommendation server 100 may be connected by a bus 170 to communicate with each other.

FIG. 6 illustrates the care device recommendation server 100 as an embodiment, but the present invention is not limited thereto. For example, a plurality of user terminals and devices may include the components of FIG. 6.

The methods according to the embodiments of the present disclosure may be implemented in the form of a program command that can be executed through various computer means and recorded in a computer-readable medium. The computer-readable medium can store program commands, data files, data structures or combinations thereof. The program commands recorded in the medium may be specially designed and configured for the present disclosure or be known to those skilled in the field of computer software.

Examples of a computer-readable recording medium may include hardware devices such as ROMs, RAMs and flash memories, which are specially configured to store and execute program commands. Examples of the program commands may include machine language code created by a compiler and high-level language code executable by a computer using an interpreter and the like. The hardware devices described above may be configured to operate as at least one software module to perform the operations of the invention, and vice versa.

In addition, the above-described method or apparatus may be implemented by combining all or part of constructions or functions thereof, or the constructions or functions may be separately implemented.

Although the present invention has been described above with reference to the embodiments of the present invention, those skilled in the art may variously modify and change the present invention without departing from the spirit and scope of the present invention as set forth in the claims below.

DESCRIPTION OF SYMBOLS

100: care device recommendation server
200: user terminal
300: skin measurement device

The invention claimed is:
1. A care device recommendation server comprising:
a memory; and
a processor, wherein the processor is configured to:
obtain face images of the user from a skin measurement device comprising a camera and a display;
determine a first skin condition of the user corresponding to a first time point at which the face images are obtained, based on the obtained the face images;
determine the skin care device for the user among a plurality of care devices comprised in a care device DB based on the determined first skin condition;
provide a first control value of the skin care device corresponding to the first skin condition to each of a user terminal of the user and the skin measurement device;
remotely control the care device such that the skin care device is driven by the control value;
provide information about a previous skin condition of the user, which corresponds to each of the face images of the user obtained from the memory, to the user terminal;
list previous skin condition images of the user in time series and provide the listed previous skin condition images to the user terminal;
calculate composite scores on skin conditions corresponding to the previous skin condition images; and determine total scores of the calculated individual scores as the composite scores and provide the determined composite scores to the user terminal, wherein when the composite scores are calculated, an individual score for each item of skin wrinkles, pore state, pigmentation, dark circles, and redness of the user is calculated.

2. The care device recommendation server according to claim 1, wherein the processor is configured to:

predict a second skin condition of the user corresponding to a second time point after a preset time from the first time point;

determine the second skin condition of the user corresponding to the second time point based on the first skin condition, a seasonal change between the first time point and the second time point, and an aging degree corresponding to an age of the user up to the second time point;

determine a first date corresponding to the first time point and a second date corresponding to the second time point;

calculate an expected change in temperature and an expected change in humidity based on a first annual average weather corresponding to the first date and a second annual average weather corresponding to the second date; and determine a first skin change degree of the user according to the seasonal change based on the calculated expected temperature change and the calculated expected humidity change.

3. The care device recommendation server according to claim 2, wherein the processor is configured to:

determine an expected aging degree of the user from the first time point to the second time point based on an age of the user and an average aging rate corresponding to the user's age; and determine a second skin change degree according to aging of the user based on the determined expected aging degree.

4. The care device recommendation server according to claim 1, wherein the processor is configured to:

provide information about an improved skin condition of the user, expected when the skin care device is used with the first control value, to the user terminal;

obtain an input signal, which indicates a period of use of the skin care device, from the user terminal, determine a user's skin condition improvement degree predicted when the skin care device is used for the period; and provide information about an improved skin condition of the user based on the skin condition improvement degree to a user terminal.

* * * * *